United States Patent [19]

Assmus et al.

[11] Patent Number: 6,063,399
[45] Date of Patent: May 16, 2000

[54] ADHESIVE BINDERS FOR DERMAL OR TRANSDERMAL THERAPY SYSTEMS

[75] Inventors: Manfred Assmus, Bickenbach; Thomas Beckert, Darmstadt; Guenter Bergmann, Gross-Krotzenburg; Stephanie Kaehler, Bensheim; Hans-Ulrich Petereit, Darmstadt, all of Germany

[73] Assignee: Roehm GmbH Chemische Fabrik, Darmstadt, Germany

[21] Appl. No.: 08/995,986

[22] Filed: Dec. 22, 1997

[30] Foreign Application Priority Data

Dec. 20, 1996 [DE] Germany ............... 196 53 605

[51] Int. Cl.⁷ ............... A61K 9/70; A61F 13/02
[52] U.S. Cl. ............... 424/448; 424/449; 424/443
[58] Field of Search ............... 424/448, 443, 424/449; 156/327

[56] References Cited

U.S. PATENT DOCUMENTS

| | | | |
|---|---|---|---|
| 4,826,686 | 5/1989 | Brantl | 424/448 |
| 4,876,092 | 10/1989 | Mizobuchi | 424/435 |
| 5,133,970 | 7/1992 | Petereit | 424/443 |
| 5,296,512 | 3/1994 | Beier | 523/111 |
| 5,310,559 | 5/1994 | Shah | 424/448 |
| 5,456,745 | 10/1995 | Roreger | 106/128 |
| 5,730,999 | 3/1998 | Lehmann | 424/443 |

*Primary Examiner*—Thurman K. Page
*Assistant Examiner*—Brian K. Seidleck
*Attorney, Agent, or Firm*—Oblon, Spivak, McClelland, Maier & Neustadt, P.C.

[57] ABSTRACT

An adhesive binder for dermal or transdermal therapy systems consists of the following components:

(a1) 55–99.9 wt. % of a (meth)acrylate copolymer of a structural (meth)acrylate or a functional (meth)acrylate monomer, wherein the functional monomer has a tertiary or quaternary amino group, (a2) 0.1–45 wt. % of an acid group-containing acrylate or (meth)acrylate polymer or copolymer, and (b) 25–80 wt. % of a plasticizer, based on the sum of (a1) and (a2).

8 Claims, No Drawings

ADHESIVE BINDERS FOR DERMAL OR TRANSDERMAL THERAPY SYSTEMS

BACKGROUND OF THE INVENTION

1. Field of the Invention

The present invention relates to an adhesive binder for dermal or transdermal drugs.

2. Description of the Background

European Patent No. 415,055 discloses water-soluble, pressure-sensitive skin adhesives. They consist of the salt of an uncrosslinked copolymer prepared by reacting an amino group-containing, monoethylenically unsaturated, radically polymerizable monomer and at least one alkyl ester of acrylic and/or methacrylic acid. The formulation comprises the salt of at least one higher organic carboxylic acid of 8–20 carbon atoms or a mixture of such a higher carboxylic acid with up to 30 mol. % (of the anionic equivalent) of medium carboxylic acids and contains a fraction of the amino group-containing monomer in the range of 30–80 wt. %, based on the weight of the copolymer, and is soluble in water in the salt form.

U.S. Pat. No. 3,321,451 describes washable skin adhesives based on amino group-containing (meth)acrylate copolymers, wherein the amino groups are partially present as the salt of an acid anion.

European Patent Application No. 164,669 describes a method for the coating of medications with (meth)acrylate copolymers, which contain monomers with tertiary amino groups, wherein they can be converted into the salt form by means of mineral acids or organic acids such as acetic acid or citric acid. The coatings should be as nontacky as possible to avoid a cementing of the medications.

European Patent Application No. 354,364 describes the use of amino group-containing copolymers in aqueous preparation as adhesives. The amino groups present in the copolymer are in part neutralized by acids such as formic acid or acetic acid.

European Patent Application No. 315,218 describes pharmaceutical compositions for the transdermal, systemic administration of pharmacologically active substances, which compositions comprise pharmacologically active substances in a reservoir which contains a polyacrylate polymer with cationic characteristics. Additives, such as plasticizers or surfactants, can be present in quantities up to 50 wt. %. The pharmaceutical composition can also be provided with an adhesive layer, so as to achieve a good adhesion to the skin.

European Patent Application No. 617,972 describes stratified dermal, therapeutic systems with delayed release of an active substance, which consists of mixtures of poly(methy) acrylates. The system is prepared from a melt. The poly (meth)acrylate component contains functional group containing (meth)adrylate monomer and also another poly (meth)acrylate monomer which does not contain or contains only inconsiderable quantities of a functional group. The poly(meth)acrylate component essentially regulates the flow behavior of the polymeric adhesive layer.

SUMMARY OF THE INVENTION

Accordingly, one object of the present invention is to provide an improved adhesive binder for pharmaceutical preparations, which has a high degree of hydrophilicity and thus a good water vapor permeability. At the same time, the binder should not only have a high adhesive force, but also a low cold flow of at least about 3 in the scale of cold flow shown infra.

Briefly, this object and other objects of the present invention as hereinafter will become more readily apparent can be attained by an adhesive binder for dermal or transdermal therapy systems, which consists of following components:

(a1) 55–99.9 wt. % of a (meth)acrylate copolymer of a structural (meth)acrylate or a functional (meth)acrylate monomer, wherein the functional monomer has a tertiary or quaternary amino group, (a2) 0.1–45 wt. % of an acid group-containing acrylate or (meth)acrylate polymer or copolymer, and (b) 25–80 wt. % of a plasticizer, based on the sum of (a1) and (a2).

DETAILED DESCRIPTION OF THE PREFERRED EMBODIMENTS

Adhesive binders for pharmaceutical purposes, which are based on (meth)acrylate copolymers with basic groups in combination with plasticizers and with acid group-containing (meth)acrylate copolymers are known as disclosed in European Patent Application No. 617,972.

A basic problem with pharmaceutical adhesive binders is the water vapor permeability. If this is not sufficient, then the compatibility on the skin is impaired. Furthermore, there is the danger that the preparations, for example, skin adhesive patches, dry too rapidly. This phenomenon adversely affects the controlled release of active substance.

The determination of the adhesive strength of a sample is carried out by removal of a 50 mm wide strip, preferably of aluminum, coated with the adhesive binder, from a VA (expansion unknown) steel plate with the simultaneous measurement of the force needed to do so. The method is based on the European Pharmacopoeia (peel method).

The minimum adhesive force needed for patches can be defined differently in accordance with the application purpose. In accordance with the invention, this value is at least 10 N/50 mm.

Another criterion of the adhesive is the so-called cold flow. The "cold flow" of an adhesive is understood to mean an unsatisfactory adhesion with a force effect parallel to the adhesive surface. On human skin, excessively high cold flow means that a patch migrates while it is being worn and leaves behind dark edges or causes folds. This is disadvantageous, in particular with active substance-containing adhesive layers, because the active substance intake into the body becomes uncontrollable in this way.

The cold flow is measured in technology according to defined conventional methods, for example, PSTC-7 or AFERA 4012-P1.

For human medical purposes, however, it is more logical to take into consideration "natural" test conditions on the human skin (degree of heat of the skin, moisture). Furthermore, the influence of different types of skin should be taken into consideration. To quantify cold flow on the human skin, the following method, for example, can be used.

A group of test subjects wears test patches, under constant conditions, for 24 h. Afterwards, the migration or the slipping of the patches is measured in millimeters and is evaluated, in the following manner, with respect to the cold flow.

| Classification: | | |
|---|---|---|
| Very good | -5- | 0 mm slippage |
| Good | -4- | 1 mm slippage |
| Medium | -3- | 2–3 mm slippage |
| Poor | -2- | 4–6 mm slippage |
| Very poor | -1- | Patch produces folds. |

Surprisingly, it has now been discovered that an improved dermal and transdermal adhesive binder can be prepared as described above. It is assumed that the advantages achieved in the present invention result from the influence of each component of the composition on the composition.

Component (a1)

Component (a1) is a (meth)acrylate copolymer of a structural (meth)acrylate monomer or a functional (meth)acrylate monomer, wherein the functional group has a tertiary amino or ammonium group or a quaternary ammonium group.

Among others, known copolymers that are within the scope of the definition of copolymer (a1) have been used for a long time as drug coatings, under the product names EUDRAGIT$^R$ E, EUDRAGIT$^R$ RS, and EUDRAGIT$^R$ RL.

Structural acrylate or methacrylate monomers do not have any other functional radicals, aside from the vinyl function. Structural acrylic or methacrylate monomers include, for example, $C_1$–$C_4$ alkyl esters of acrylic and methacrylic acid. Methyl acrylate, ethyl acrylate, butyl acrylate, butyl methacrylate, and methyl methacrylate are preferred.

"Functional monomers are understood to mean (meth) acrylate compounds, which have other functional groups aside from the vinyl function.

Dimethylaminoethyl methacrylate is particularly preferred as a monomer which has a functional tertiary amino group. The content of the functional monomer having a tertiary amino group in the copolymer advantageously ranges form 30–70 wt. %, preferably 40–60 wt. %.

2-Trimethylammoniumethyl methacrylate chloride is particularly preferred as a monomer having a functional quaternary ammonium group. The content of the functional monomer having a quaternary ammonium group in the copolymer preferably ranges from 2–15 wt. %.

A (meth)acrylate copolymer, corresponding to component (a1), with tertiary amino groups can be synthesized, for example, from 25 wt. % methyl methacrylate, 25 wt. % butyl methacrylate, and 50 wt. % dimethylaminoethyl methacrylate (EUDRAGIT$^R$ E 100).

A (methy)acrylate copolymer, corresponding to component (a1), with quaternary amino groups can be synthesized, for example, from 60 wt % methyl methacrylate, 30 wt. % ethyl acrylate, and 10 wt. % 2-trimethylammoniumethyl methacrylate chloride (EUDRAGIT$^R$ RL 100).

Another preferred (meth)acrylate copolymer corresponding to component (a1) with a quaternary amino group can be synthesized, for example, from 65 wt. % methyl methacrylate, 30 wt. % ethyl acrylate, and 5 wt. % 2-trimethylammoniumethyl methacrylate chloride (EUDRAGIT$^R$ RS 100).

Copolymers (a) are obtained in a known manner by radical bulk, solution, bead, or emulsion polymerization. They can be formulated present as an extruded granulate, a ground material, a powder, a solution, or a dispersion.

Component (a2)

Component (a2) can be acid group-containing acrylate or (meth)acrylate polymers or copolymers. Polyacrylic acid ($^R$Carbopol), for example, is suitable. Preferred copolymers are, however, structural and functional (meth)acrylate monomers. Structural acrylate or methacrylate monomers include, for example, $C_1$–$C_4$ alkyl esters of acrylic or methacrylic acid. Methyl acrylate, ethyl acrylate, butyl acrylate, and methyl methacrylate are preferred. Methacrylic acid is particularly preferred as a monomer with functional acid groups.

A copolymer within the scope of component (a2) can be synthesized, for example, from 30–70 wt. % ethyl acrylate or methyl methacrylate and 70-30 wt. % methacrylic acid.

For the invention under consideration, it is essential that components (a1) and (a2) be present in the indicated amounts. The fraction of component (a1) should range from 55–99.9 wt. %, preferably 85–99.9 wt. %. The amount of (a1) is supplemented by component (a2) to 100 wt. %. If the fraction of acid group-containing copolymer (a2) is less than 0.1 wt. %, then the adhesive force is not yet sufficient, as a rule. If the fraction is above 45 wt. %, the disadvantage which results is that the processability can be impaired. The fraction of component (a2) ranges preferably from 15-0.1 wt %.

Component (b), a plasticizer, must be present in an amount of at least 25 wt. % and at most 80 wt. %, preferably 30–60 wt. %, based on the sum of components (a1) and (a2). If it is used in an amount of less than 25 wt. % plasticizer, the composition normally does not sufficiently adhere to the skin. If the fraction is above 80 wt %, release of the active substance normally is only controlled with difficulty.

Substances suitable as plasticizers normally have a molecular weight ranging from 100–20,000 and contain one or more hydrophilic groups in the molecule, for example, hydroxy, ester, or amino groups. Examples of suitable plasticizers include alkyl citrate, glycerol ester, alkyl phthalate, alkyl sebacate, sucrose ester, sorbitan ester, dibutyl sebacate, and polyethylene glycols 4,000–20,000. Preferred plasticizers are triethyl citrate and acetyltriethyl citrate.

The addition of the plasticizer permits the adaptation of physical characteristics to the requirements of the individual medications, so that sufficient adhesion forces are attained at room or body temperature.

Furthermore, in the indicated ratios, the plasticizers can advantageously decrease the melt viscosity of the polymers employed, in the liquid state. At room temperature, softening effects can be recognized. Moreover, influences on the release behavior of embedded active substances is possible.

Variations of the composition make it possible, if necessary, to compensate for undesired effects of medication-affected additives. The adhesive binders of the invention can optionally contain other additives in small amounts, if the special formulation requires it: neutral polymers, tackifiers, stabilizers, dyes, antioxidants, wetting agents, pore-forming agents, moisturizers, complexing agents, and so forth.

Production Methods

The production of the binder depends on the form of the polymer used. Solid substances can be used directly by mixing with the additives in suitable mixers, kneaders, or extruders, which are heatable and can be evacuated. The extruder is single-screw or preferably twin-screw, in order to enable suitable mixing and transporting characteristics.

The processing temperature depends on the melting characteristics of the materials and is preferably ranges from 20–200° C. Limiting factors are the thermal stability of substances used. Solid additives can be mixed with the polymer before extrusion. Liquid additives are added to approximately half the extrusion path of the melt and bring about a lowering of the viscosity and a reduction of the temperature.

Polymer solutions or dispersions are mixed with the additives, so that they can be dissolved or suspended. The binder is obtained from these solutions, dispersions, or suspensions by drying to thin film layers.

Processing

Coating, granulation, sheathing, or embedding takes place by the organic dissolution or aqueous dispersion of suitable auxiliaries.

The use of melts is limited to substances with defined melting points in the range of processing temperatures. Low melt viscosities are usually required for processing.

In one embodiment, the solid adhesive binder in accordance with the invention is mixed with the powders and mixed with suitable solvents or the mixture is melted.

Preferably from solution or suspension or directly from the melt, one obtains adhesive layers which fix the system on the skin. The layers are particularly compatible because of their hydrophilicity as they are spread out, for example, as films, fabrics, or fleeces on flat carriers after drying or cooling. The coating takes place discontinuously in the laboratory by a doctor or in a pilot plant and production, continuously by a roll doctor or roller application. Immediately after the coating, a weakly adhering, often siliconized cover film, which is removed before use, is added.

The obtained agglomerates or adhesive layers can be further processed to a medicinal formulation for application. It is thereby possible to work drugs into the formulation during the production of the adhesive binder. These active substances are then fixed in a particulate or dissolved form. Release of the active substance is possibly influenced by the adhesive binder, which is considered in the formulation of a medication.

Formulation of the Medications

The drugs used in the present invention are those which are to be applied on or in the human or animal body, so as to:

1. heal, alleviate, prevent, or recognize diseases, suffering, body injuries, or disease-related complaints;
2. recognize the nature, the state, or the functions of the body or mental states;
3. replace active substances or body fluids produced by the human or animal body;
4. fend off, eliminate, or render harmless pathogens, parasites, or substances alien to the body;
5. influence the nature, the state, or the functions of the body or mental states.

Common drugs can be found in reference works such as the Pharmacopoeia or the Merck Index.

In accordance with the invention, any active substance can be sued, which brings about the desired therapeutic effect in the sense of the above definition or have a sufficient thermal stability.

Without claim to completeness, important examples (groups and individual substances) include the following:
analgesics, antiallergic agents, antiarrhythmic agents
antibiotics, chemotherapeutics, antidiabetic agents, antidotes, antiepileptic drugs, antihypertensive agents, antihypotonic agents, anticoagulants, antimycotic agents, antiphlogistics, beta-receptor blockers, calcium antagonists, and ACE inhibitors, broncholytic/antiasthmatic agents, cholinergic agents, corticoids (internal), dermatic agents, diuretics, enzyme inhibitors, enzyme preparations, and
transport proteins, expectorants, geriatric medicines, gout remedies, influenza medicines, hormones and their inhibitors, hypnotics/sedatives, cardiacs, lipid-lowering substances, parathyroid hormones/calcium metabolism regulators, psychopharmacological agents, sexual hormones, and their inhibitors, spasmolytic drugs, sympatholytic agents, sympathomimetic drugs, vitamins, wound treatment agents, cytostatic agents.

Medications can be produced from the intermediate stages prepared in accordance in the invention by the usual processing techniques.

Carriers coated with the adhesive binder are normally present on rollers protected by cover films (release liners). Individual patches of the required size are cut or punched from these sheets and packed individually.

The coating of flat carriers with polymer-containing liquids is described, for example, by J. Mass and H. Schmidt in Coating Technology for Transdermal Drug Delivery Systems, Medical Device Technology, Issue 3/41990, pp. 46–50.

Characteristics relevant for the application, required tests, and specifications are listed in pharmacopoeias.

Details can be found in current textbooks, such as:
R. Voigt (1984): Lehrbuch der pharmazeutischen Technologie [Textbook of Pharmaceutical Technology]; Verlag Chemie Weinheim-Beerfield [sic; Deerfield] Beach/Florida-Basel.
H. Sucker, P. Fuchs, P. Speiser: Pharmazeutische Technologie [Pharmaceutical Technology], Georg Thieme Verlag Stuttgart (1991), especially chapters 15 and 16, pp. 626–642.
A. R. Gennaro (Editor), Remington's Pharmaceutical Sciences, Mack Publishing Col., Easton Pa. (1985), chapter 88, pp. 1567–1573.
K. Heilmann: Therapeutische Systeme [Therapeutic Systems], Ferdinand Euler Verlag, Stuttgart, pp. 52–57.
R. Brandau and B. H. Lippold (1982): Dermal and Transdermal Absorption. Wissenschaftliche Verlagsgesellschaft mbH, Stuttgart, pp. 171–200.

Having generally described this invention, a further understanding can be obtained by reference to certain specific examples which are provided herein for purposes of illustration only and are not intended to be limiting unless otherwise specified.

EXAMPLE 1

Preparation of an Adhesive layer for Dermal and Transdermal Therapy Systems from Organic Solution A 40 g amount of a copolymer (a1) of 25 wt. % methyl methacrylate 25 wt. %, butyl methacrylate, and 50 wt. % dimethylaminoethyl methacrylate (tradename $^R$EUDRAGIT E 100) is dissolved in a mixture of 24 g acetone, 12 g ethanol, and 3 g isopropanol. A 20 g amount of the plasticizer acetyltriethyl citrate (component b) and, at a high rate of stirring, 0.1 g of a copolymer (a2) of 50 wt. % methyl methacrylate and 50 wt. % methacrylic acid (tradename $^R$EUDRAGIT L 100) are worked into this solution as a 20% ethanolic solution. A 200 μm layer of the adhesive is dried at 60° C. for 10 min on a 50 μm thick aluminum film. Round patches with a diameter of 43 mm are punched out from the film. These samples adhere firmly to the human skin and can be removed free of residue. A 300 μm thick layer of the adhesive is spread over the surface of a 50 μm thick aluminum film with a doctor at 120° C. and cooled. The adhesive layer has an adhesive strength of 63 (N/50 mm), measured according to the peel method, Eur. Ph. II.

EXAMPLE 2

Preparation of an Adhesive Layer for Dermal and Transdermal Therapy Systems from a Melt The melting process is carried out in a measuring kneader. The mixing vat is preheated to 120° C. At this temperature, which is maintained during the entire process time, 100 g
$^R$EUDRAGIT E 100, 50 g triethyl citrate, and 1.5 g
$^R$EUDRAGIT L 100 are worked in, in portions. The rate of
stirring is 25 rpm. This solution is coated as described in
Example 3. Round patches with a diameter of 43 mm are
punched out from the film. These samples adhere firmly to
the human skin and can be removed free of residue. A 300
μm thick layer of the adhesive is spread over the surface of
a 50 μm thick aluminum film with a doctor at 120° C. and
cooled. The adhesive layer has an adhesive strength of 58
(N/50 mm), measured according to the peel method, Eur. Ph.
II.

EXAMPLE 3

Preparation of an Adhesive Layer for Dermal and
Transdermal Therapy Systems from a Melt The mixing vat is preheated to 120° C. in a heatable
kneader with a double jacket. At this temperature, which is
maintained during the entire process time, 400 g,
$^R$EUDPAGIT E 100 , 160 g triethyl citrate, and 40 g
$^R$EUDRAGIT L 100-55 (copolymer (a2) of 50 wt. % ethyl
acrylate and 50 wt. % methacrylic acid) are worked in, in
portions. The rate of stirring is 25 rpm. A clear, slightly
yellowish melt is spread on an aluminum foil to form an
approximately 150 μm layer with a doctor on a heated table.
Round patches with a diameter of 43 mm are punched out
from the film. These samples adhere firmly to the human
skin and can be removed free of residue. A 300 μm thick
layer of the adhesive is spread over the surface of a 50 μm
thick aluminum film with a doctor at 120° C. and cooled.
The adhesive layer has an adhesive strength of 69 (N/50
mm), measured according to the peel method, Eur. Ph. II.

EXAMPLE 4

Preparation of an Adhesive Layer for Dermal and
Transdermal Therapy Systems from a Melt The mixing vat is preheated to 120° C. in a heatable
kneader with a double jacket. At this temperature, which is
maintained during the entire process time, 180 g
$^R$EUDRAGIT RS 100, 123.6 g triethyl citrate, and 120.6 g
$^R$EUDRAGIT L 100 (copolymer (a2) of 50 wt. % methyl
methacrylate and 50 wt. % methacrylic acid) are worked in,
in portions. The rate of stirring is 25 rpm. A yellowish-white
melt is spread over the surface of an aluminum foil to form
an approximately 300 μm layer with a doctor on a heated
table. Round patches with a diameter of 43 mm are punched
out from the film. These samples adhere firmly to the human
skin and can be removed free of residue.

A 300 μm thick layer of the adhesive is spread over the
surface of a 50 μm thick aluminum film with a doctor at 120°
C. and cooled. The adhesive layer has an adhesive strength
of 53 (N/50 mm), measured according to the peel method,
Eur. Ph. II.

COMPARISON EXAMPLES

Preparations in which the quantitative fractions were
varied in a manner not consistent with the invention
(Comparisons 1–5) were tested with respect to
hydrophilicity, adhesive strength, and cold flow. The results
are compiled in Table I in comparison to Examples 1–4.

|  | a1 Wt. % | a1 Wt. % | b Wt. % b:a1 + a2 | Hydrophilicity WDD DIN 53 122 | Adhesion Strength (N/50 mm) | Cold Flow |
|---|---|---|---|---|---|---|
| Ex 1 | 99.75(E) | 0.25 L100 | 49.9 ATEC | 470 | 83 | 3 |
| Ex 2 | 98.50(E) | 1.50 L100 | 49.2 TEC | 510 | 58 | 3 |
| Ex 3 | 90.00(E) | 10.0 L55 | 36.3 TEC | 590 | 69 | 5 |
| Ex 4 | 60.00(RS) | 40.0 L100 | 41.2 TEC | 390 | 52 | 3 |
| C. Ex 1 | 100.00(RS) | — | 20.0 TEC | 250 | <10 | —** |
| C. Ex 2 | 100.00(RL) | — | 50.0 TEC | —** | <10 | —** |
| C. Ex 3 | 90.00(E) | 10.0 L100 | 20.0 TEC | 540*** | <10 | —** |
| C. Ex 4 | 50.00(RS) | 50.0 L100 | 50.0 TEC | 410 | 53 | 2 |
| C. Ex 5 | 100.00(RL) | — | 80.0 TEC | —** | <10 | —** |

*Scale of 1 = very poor to 5 = very good
**Not dertermined, since adhesive strength to too small
***Estimated
E = copolymer of 25 wt. % methyl methacrylate, 25 wt. % butyl methacrylate, and 50 wt. %
dimethylaminoethyl methacrylate; (EUDPAGIT$^R$ E 100, Rohm GmbH, D-64293 Darmstadt,
Germany);
RS = copolymer of 65 wt. % methyl methacrylate, 30 wt. % ethyl acrylate, and 5 wt. %
2-trimethylammonium ethyl methacrylate chloride (EUDPAGIT$^R$ RS, Rohm GmbH, D-64293
Darmstadt, Germany);
RL = copolymer of 60 wt. % methyl methacrylate, 30 wt. % ethyl acrylate, and 10 wt. %
2-trimethylammoniumethyl methacrylate chloride (EUDPAGIT$^R$ RL, Rohm GmbH, D-64293
Darmstadt, Germany);
ATEC = acetyltriethyl citrate;
TEC = triethyl citrate;
L 100 = copolymer of 50 wt. % methyl methacrylate and 50 wt. % methacrylic acid
(EUDRAGIT$^R$ L 100);
L55 = copolymer of 50 wt. % ethyl acrylate and 50 wt. % methacrylic acid (EUDRAGIT$^R$ L
100-55).

German priority application 19 653 605. 7 filed Dec. 20,
1996 is hereby incorporated by reference into the present
application.

Obviously, numerous modifications and variations of the
present invention are possible in light of the above teach-
ings. It is, therefore, to be understood that within the scope of the appended claims, the invention may be practiced otherwise than as specifically described herein.

What is claimed as new and is desired to be secured as Letters Patent is:

1. An adhesive binder for dermal and transdermal therapy systems, consisting of the following components:
    (a1) 55–99.9 wt. % of a (meth)acrylate copolymer of a structural (meth)acrylate monomer or a functional (meth)acrylate monomer, wherein the functional monomer has a tertiary or quaternary amino group,
    (a2) 0.1–45 wt. % of an acrylate or methacrylate copolymer formed of 30–70 wt. % acrylate or (meth)acrylate ester monomer units and 70-30 wt. % (meth)acrylic acid monomer units or polyacrylic acid, and
    (b) 25–80 wt. % of a plasticizer, based on the sum of (a1) and (a2).

2. A method of preparing a transdermal therapy system, comprising:
    coating, spraying or spreading solutions, dispersions, suspensions or melts of a pharmaceutically active substance in the adhesive binder of claim 1, and subsequently drying or cooling the mixture.

3. The adhesive binder according to claim 1, wherein the quantity of the plasticizer (b) is 30–60 wt. %, based on the sum of (a1) and (a2).

4. The adhesive binder according to claim 1, wherein the structural (meth)acrylate monomer of component (a1) is a $C_{1-4}$ alkyl ester of (meth)acrylic acid.

5. The adhesive binder according to claim 1, wherein said copolymer component (a2) contains a structural monomer which is a $C_{1-4}$ alkyl (meth)acrylate.

6. The adhesive binder according to claim 5, wherein the structural monomer of said copolymer component (a2) is copolymerized with methacrylic acid.

7. The adhesive binder according to claim 1, wherein said plasticizer is a member selected from the group consisting of alkyl citrate, glycerol ester, alkyl phthalate, alkyl sebacate, sucrose ester, sorbitan ester, dibutyl sebacate, and polyethylene glycols having molecular weights ranging from 4,000 to 20,000.

8. The method according to claim 2, wherein the pharmaceutically active substance is nicotine, glycerol trinitrate, scopolamine, clonidine, fentanyl, estradiol, testosterone, oxibutynin, diclofenac, ibuprofen, ketoprofen, diltiazem, propranolol, albuterol, alprazolam, amethocaine, atenolol, benzoporphyrin, buprenorphine, calcitonin, dithranol, diphencyprone, peptides, eptazocine, ethinyl estradiol, methotrexate, or naloxone.

* * * * *